(12) United States Patent
Chen et al.

(10) Patent No.: US 11,083,558 B2
(45) Date of Patent: Aug. 10, 2021

(54) CATCHER

(71) Applicant: Lifetech Scientific (Shenzhen) Co., Ltd., Shenzhen (CN)

(72) Inventors: Zhuo Chen, Shenzhen (CN); Hong-bing Luo, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 237 days.

(21) Appl. No.: 15/781,962

(22) PCT Filed: Aug. 16, 2016

(86) PCT No.: PCT/CN2016/095540
§ 371 (c)(1),
(2) Date: Jun. 6, 2018

(87) PCT Pub. No.: WO2017/113810
PCT Pub. Date: Jul. 6, 2017

(65) Prior Publication Data
US 2018/0360587 A1    Dec. 20, 2018

(30) Foreign Application Priority Data

Dec. 31, 2015 (CN) .......................... 201511033591.3
Aug. 4, 2016 (CN) .......................... 201610638920.5

(51) Int. Cl.
*A61F 2/01* (2006.01)
*A61B 17/221* (2006.01)
(Continued)

(52) U.S. Cl.
CPC ...... *A61F 2/01* (2013.01); *A61B 2017/00358* (2013.01); *A61B 2017/2212* (2013.01);
(Continued)

(58) Field of Classification Search
CPC . A61B 17/22031; A61F 2/01; A61F 2002/016
See application file for complete search history.

(56) References Cited

U.S. PATENT DOCUMENTS 6,296,622 B1 * 10/2001 Kurz ................ A61B 17/12022
604/93.01
9,101,383 B1 * 8/2015 Dostal .................... A61B 17/50
(Continued)

OTHER PUBLICATIONS

International Search Report dated Nov. 29, 2016 for corresponding PCT Application No. PCT/CN2016/095540.

*Primary Examiner* — Richard G Louis
(74) *Attorney, Agent, or Firm* — Raymond Sun (57) ABSTRACT

Disclosed is a catcher (100), comprising an catching ring (11) and at least one connecting rod (15), wherein both ends of the connecting rod (15) are connected to the catching ring (11), and the connecting line between the two ends of the connecting rod (15) is located within the catching ring (11). Compared with catching loops in the prior art, the catching ring (11) of the catcher (100) is a ring structure supported by the connecting rod (15), thereby having a relatively high stability and not easily being deformed under erosion by a blood flow, so as to facilitate accurate positioning by a doctor during clinical operations and improve the success rate of withdrawal.

20 Claims, 6 Drawing Sheets

(51) Int. Cl.
*A61B 17/00* (2006.01)
*A61B 17/22* (2006.01)

(52) U.S. Cl.
CPC ..... *A61B 2017/22035* (2013.01); *A61F 2/011* (2020.05); *A61F 2002/016* (2013.01); *A61F 2210/0014* (2013.01)

(56) References Cited

U.S. PATENT DOCUMENTS

| | | | | |
|---|---|---|---|---|
| 2004/0073242 | A1* | 4/2004 | Chanduszko | A61B 17/0057 606/157 |
| 2007/0265700 | A1* | 11/2007 | Eliasen | A61F 2/246 623/2.1 |
| 2009/0118760 | A1* | 5/2009 | Clausen | A61B 17/221 606/200 |
| 2009/0157115 | A1 | 6/2009 | Fleming | |
| 2016/0022291 | A1* | 1/2016 | Johnson | A61B 8/12 606/113 |

* cited by examiner

CATCHER

TECHNICAL FIELD

The present disclosure relates to the field of medical devices, and more particularly relates to a catcher.

BACKGROUND ART

Pulmonary embolism (PE) is a common disease which would cause a high mortality rate. According to the statistical data, the mortality rate caused by untreated pulmonary embolism is 20 to 30 percent. Every year, new cases make up about 0.2 percent of the population, that is, 2,700,000 new cases of pulmonary embolism in China on the basis of a population of 1.35 billion. It is clinically proven that a vena cava filter (hereinafter referred to as "filter") is a safe and effective measure for preventing the pulmonary embolism, which may reduce the incidence rate of the pulmonary embolism. After the filter is implanted into an inferior vena cava, it prevents a thrombus falling off from a low limb from reaching the lung along the blood flow, thereby preventing the pulmonary embolism.

Clinically, after the filter is implanted into the body of a patient for a period of time, the risk of occurrence of the pulmonary embolism will be reduced or disappears along with the treatment; and at the moment, the filter needs to be taken out of the body of the patient to prevent long-term implantation risks, so that a device for withdrawing the vena cava filter is needed.

Figure 1:
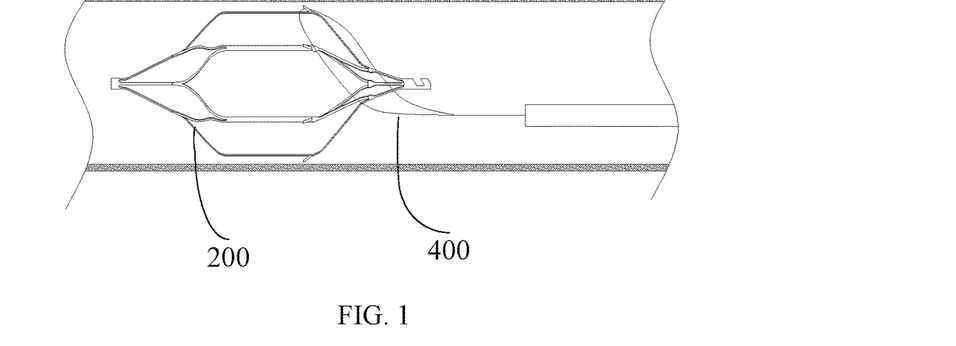
FIG. 1 is a schematic diagram showing the catching of a filter by an existing catcher.

With reference to FIG. 1, for clinical practice at the present time, a catching loop 400 is used for withdrawing the vena cava filter 200. However, this catching loop 400 is relatively soft during clinical use, and would be easy to deform and be difficult to locate under erosion by blood flow, thereby prolonging the time needed for withdrawal of the filter, and increasing the surgical risk.

SUMMARY OF THE INVENTION

Based on the above-mentioned problem, it is necessary to provide a catcher which does not deform easily, but which is easy to locate under erosion by blood flow.

The present disclosure provides a catcher, including a catching ring. The catcher further includes at least one connecting rod; two ends of the connecting rod are connected with the catching ring, and a connecting line of the two ends of the connecting rod is located in the catching ring.

In one embodiment, the catcher further includes an operating rod which is connected to the middle portion of the connecting rod or is connected with one end of the connecting rod.

The present disclosure provides a catcher, including a catching ring. The catcher includes multiple connecting rods; one end of each connecting rod is connected with the catching ring, and the other end of each of the connecting rods is gathered together.

In one embodiment, the catcher further includes an operating rod, and all the connecting rods are gathered together, and then are connected with the operating rod.

In one embodiment, a projection of the catching ring on a section perpendicular to a lengthwise direction of the operating rod surrounds a projection of the distal end of the operating rod on the same section.

In one embodiment, the multiple connecting rods and the catching ring are located in the same plane; the catching ring is a circular ring; and the connecting line of two ends of each connecting rod forms the radius of the catching ring.

In one embodiment, the multiple connecting rods and the catching ring are located in the same plane; the catching ring is an elliptical ring; and the connecting line of two ends of at least one connecting rod forms a long axis or a short axis of the catching ring.

In one embodiment, an included angle between the connecting line of two ends of each connecting rod and the longitudinal central axial line of the operating rod ranges from 30 degrees to 150 degrees.

In one embodiment, the included angle between the connecting line of two ends of each connecting rod and the longitudinal central axial line of the operating rod is 90 degrees.

In one embodiment, 2 to 6 connecting rods are provided.

In one embodiment, the multiple connecting rods are centrally and symmetrically distributed along the longitudinal central axial line of the operating rod.

The present disclosure provides a catcher, including multiple connected catching subrings. Each catching subring includes a connecting rod and a catching section connected with the connecting rod; the connecting rods of two adjacent catching subrings at least partially share one edge; and the multiple catching sections form a catching ring of the catcher.

In one embodiment, the catcher further includes an operating rod; and the operating rod is connected with the connecting rods of the catching subrings.

In one embodiment, an included angle between each of two ends of each connecting rod of the catcher and the longitudinal central axial line of the operating rod ranges from 30 degrees to 150 degrees.

In one embodiment, the included angle between the connecting line of two ends of each connecting rod of the catcher and the longitudinal central axial line of the operating rod is 90 degrees.

In one embodiment, the diameter of a surrounding circle of the catching ring is 8 to 30 mm.

In one embodiment, one portion of the catching ring has an outward depression along a radial direction to form a catching groove.

In one embodiment, each connecting rod includes a straight section, a curved section or a polyline section.

In one embodiment, the catching ring and the connecting rods are integrated.

In one embodiment, the catcher further includes an operating rod; the operating rod includes an operating section and a soft section connected between the operating section and the catching ring; and under the action of the same external force, the soft section deforms more easily than the operating section.

In one embodiment, the soft section is a spring pipe.

In one embodiment, the soft section is connected with the connecting rods.

In one embodiment, the operating rod also includes an anti-detachment part arranged at the proximal end of the operating section.

In one embodiment, the anti-detachment part is spherical.

In one embodiment, the catcher further includes a clamping part arranged at the proximal end of the catcher; the clamping part includes a main body section having an inner cavity and a hollow clamping section which is arranged at the distal end of the main body section and is communicated with the inner cavity of the main body section; multiple slots communicated with the inner cavity of the clamping section are formed in the side wall of the clamping part; each slot penetrates through the side wall of the clamping section, and penetrates through the side wall of part of the main body section; in a natural state, the anti-detachment part may move from the distal end of the inner cavity of the clamping section to the proximal end of the inner cavity of the clamping section; under the action of a radial external force, the inner diameter of the clamping section is reduced; and the anti-detachment part is not separated from the distal end of the clamping section when being clamped by the clamping section.

In one embodiment, the inner wall of the clamping part extends towards the inner cavity of the clamping part to form a hollow annular boss; the length of the annular boss along an axial direction of the clamping part is reduced successively from outside to inside; and under the action of the radial external force, the anti-detachment part is not separated from the annular boss when being clamped by the annular boss.

Compared with the catching loops in the prior art, the catching ring of the catcher of the present disclosure is of a ring structure supported by the connecting rods, thereby having a relatively high stability and being difficult to deform under the erosion by the blood flow, so as to facilitate accurate positioning by a doctor during clinical procedures and thereby increasing the success rate of withdrawal.

DETAILED DESCRIPTION OF THE INVENTION

For the purpose of making objectives, features and advantages of the present disclosure clearer, a detailed description will be made below to specific implementation modes of the present disclosure in conjunction with corresponding drawings. Many specific details are described in the following descriptions to facilitate a full understanding of the present disclosure. But the present disclosure may be implemented in many other ways different from that described herein. Persons skilled in the art can make similar improvements without departing from the scope of the present disclosure, so that the present disclosure will not be limited by the specific embodiments disclosed below.

It should be noted that in the field of intervention, generally, the end relatively close to an operator is a proximal end, and the end relatively far away from the operator is a distal end.

Unless otherwise specified, all technical and scientific terms used herein are the same as meanings of general understandings of technical persons skilled in the art of the present disclosure. The terms used in the description of the present disclosure in this text are only to describe specific embodiments, not intended to limit the present disclosure. The terms "and/or" used in this text include any and all combinations of one or multiple relevant listed items.

Figure 2:
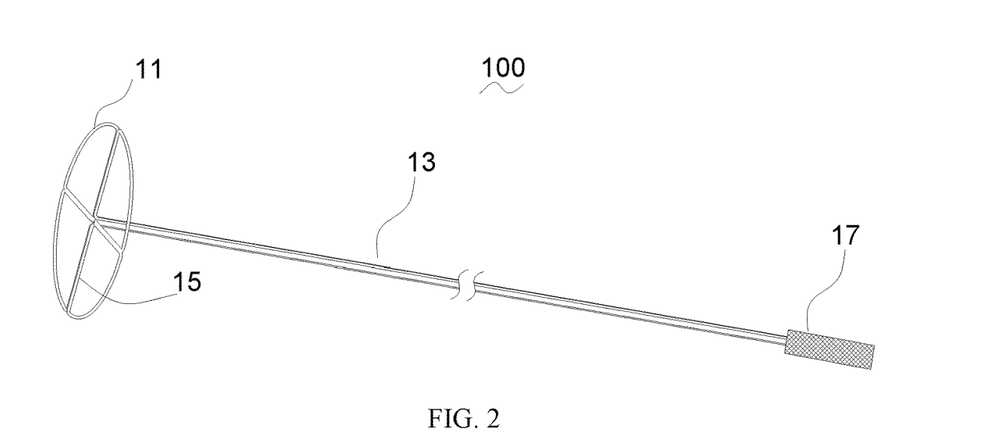
FIG. 2 is a schematic diagram of a catcher provided by one embodiment of the present disclosure.

With reference to FIG. 1 and FIG. 2 together, a catcher 100 provided by one embodiment of the present disclosure is used for catching a filter 200, and includes a catching ring 11, an operating rod 13 connected with the catching ring 11, multiple connecting rods 15 connected between the catching ring 11 and the operating rod 13, and a handle 17 connected to the proximal end of the operating rod 13. The operating rod 13 and the handle 17 are used for operating the whole catcher 100. The handle 17 is connected with the catching ring 11 through the operating rod 13.

Figure 3:
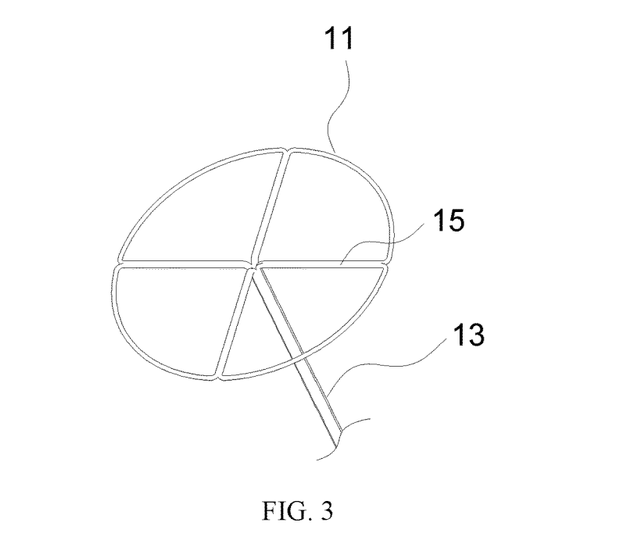
FIG. 3 is a schematic diagram from another angle of the catcher in FIG. 2.
Figure 4:
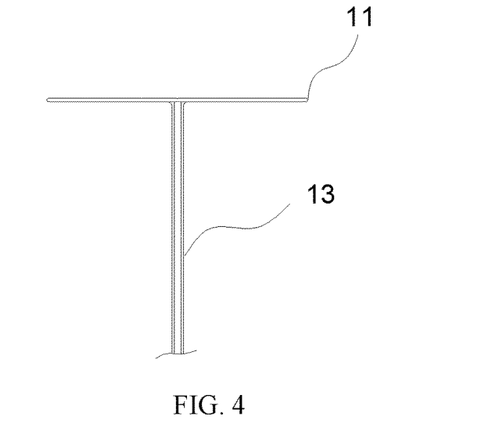
FIG. 4 is a side view of the catcher as shown in FIG. 3.
Figure 5:
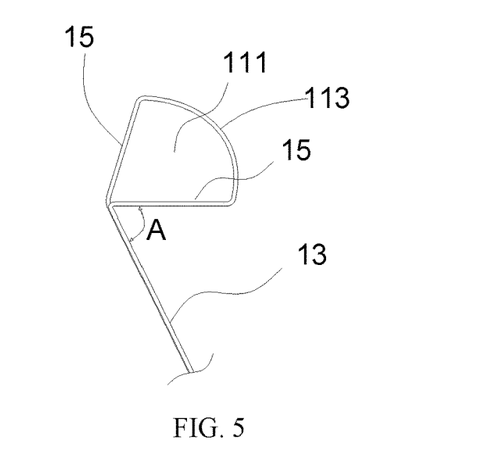
FIG. 5 is a schematic diagram of a catching subring of the catcher in FIG. 3.

With reference to FIGS. 3 to 5 together, the catching ring 11 is connected with the operating rod 13. The catching ring 11 is of an elastic closed ring structure, and the diameter of its surrounding circle is 8 to 30 mm. When the diameter of the surrounding circle of the catching ring 11 is less than 8 mm, it is more difficult for the catching ring 11 to catch the filter 200, thereby affecting the handfeel of catching the filter by the operator and reducing the surgical efficiency; when the diameter of the surrounding circle of the catching ring 11 is more than 30 mm, it is very hard to reduce the perimeter of the catching ring 11, and during the process of catching the filter 200, the catching ring 11 may easily pass through a gap between the filter 200 and a blood vessel wall to grab a fixing anchor or a fixing rod of the filter 200, thereby making it more difficult for the filter to enter a sheath, reducing the catching efficiency and prolonging the surgical time. In particularly, the "surrounding circle" in the present disclosure is a circle (namely an excircle) where all vertices of the catching ring are intersected; and in addition, if the circle where all the vertices of the catching ring are intersected does not exist, the "surrounding circle" in the present disclosure is a circle which is drawn by taking a connecting line of two points farthest to each other on the catching ring as a diameter and taking the center of the connecting line of the two points as the center of the circle. In this embodiment, a projection of the catching ring 11 on a section perpendicular to a lengthwise direction of the operating rod 13 surrounds a projection of the distal end of the operating rod 13 on the same section; the catching ring 11 is a circular ring; and the diameter of its surrounding circle is equal to that of the catching ring 11, and is 30 mm.

There are 2 to 6 connecting rods 15. One end of each connecting rod 15 is connected with the catching ring 11, and the other end of each of the multiple connecting rods 15 is gathered together. An included angle A between a connecting line of two ends of each connecting rod 15 and the longitudinal central axial line of the operating rod 13 ranges from 30 degrees to 150 degrees. In this embodiment, there are 4 connecting rods 15; the other ends of the multiple connecting rods 15 are gathered together, and then are connected with the operating rod 13; all the connecting rods 15 are straight rods, and their lengths are equal; the multiple connecting rods 15 and the catching ring 11 are located in the same plane; the connecting line of the two ends of each connecting rod forms the radius of the catching ring 11; the included angle between the connecting line of the two ends of each connecting rod and the longitudinal central axial line of the operating rod 13 is 90 degrees; and the multiple connecting rods 15 are centrally and symmetrically distributed along the longitudinal central axial line of the operating rod 13.

It can be understood that in other embodiments, the included angle between the connecting line of the two ends of each connecting rod 15 and the longitudinal central axial line of the operating rod 13 may be 30 degrees or 150 degrees. It also can be understood that in other embodiments, the operating rod 13 also may be connected to the catching ring 11, or connected to a certain connecting rod 15. It also can be understood that in other embodiments, at least one connecting rod 15 in the multiple connecting rods 15 includes a straight section, a curved section or a polyline section. It also can be understood that in other embodiments, at least one connecting rod 15 in the multiple connecting rods 15 may be a curved rod or a polyline rod. It also can be understood that in other embodiments, the lengths of the connecting lines of the two ends of at least two connecting rods 15 in the multiple connecting rods 15 may be unequal. It also can be understood that in other embodiments, the multiple connecting rods 15 and the catching ring 11 are located in the same plane; and the catching ring 11 also may be an elliptical ring, and the connecting line of the two ends of at least one connecting rod 15 forms the long axis or the short axis of the elliptical catching ring, which also may realize a function of supporting the catching ring 11 by the connecting rod 15.

It also can be understood that in other embodiments, there also may be one connecting rod 15 of the catcher 100. Two ends of the connecting rod 15 are connected with the catching ring 11, and the connecting line of the two ends of the connecting rod 15 is located in the catching ring 11, which also may realize the function of supporting the catching ring 11 by the connecting rod 15; for example, if the catching ring 11 is of a circular structure, the connecting rod 15 overlaps a certain diameter of the catching ring 11, and a joint of the connecting rod 15 and the catching ring 11 is connected with the operating rod 13, or the operating rod 13 is connected to the middle portion of the connecting rod 15, or the operating rod 13 is connected to the catching ring 11 and is far away from the connecting rod 15; for another example, if the catching ring 11 is of a square or elliptical structure or structures having other shapes, the connecting rod 15 is overlapped with a certain symmetric axis of the catching ring 11, and a joint of the connecting rod 15 and the catching ring 11 is connected with the operating rod 13, or the operating rod 13 is connected to the middle portion of the connecting rod 15, or the operating rod 13 is connected to the catching ring 11 and is far away from the connecting rod 15. It also may be understood that in other embodiments, the two ends of each connecting rod 15 in the multiple connecting rods 15 also may be connected with the catching ring 11, and the connecting line of the two ends of each connecting rod 15 is located in the catching ring 11, which may also realize the function of supporting the catching ring 11 by the connecting rods 15; for example, if multiple end portions of the multiple connecting rods 15 are distributed on the catching ring 11 in a spaced-apart manner, a joint of a certain connecting rod 15 and the catching ring 11 is connected with the operating rod 13, or the operating rod 13 is connected to the middle portion of the certain connecting rod 15; for another example, if one end of each of at least two connecting rods 15 in the multiple connecting rods 15 is gathered onto the catching ring 11, a joint of a certain connecting rod 15 and the catching ring 11 is connected with the operating rod 13, or the operating rod 13 is connected to the middle portion of the connecting rod 15, or the operating rod 13 is connected to a gathered position of the at least two connecting rods 15.

Two adjacent connecting rods 15 and a portion (namely a catching section 113), which is located between the corresponding two adjacent connecting rods 15, of the catching ring 11 form one catching subring 111 in an encircling manner, that is to say, each catching subring 111 includes the two connecting rods 15 and the catching section 113 connected between the two connecting rods 15. It can be understood that each catching subring 111 is formed by shaping a single wire made of a nickel-titanium or stainless steel material, a multi-strand wire made of the nickel-titanium or stainless steel material, or a flat band made of the nickel-titanium or stainless steel material; two adjacent connecting rods 15 of two adjacent catching subrings 111 in the multiple independently formed catching subrings 111 may at least partially share one edge through a process such as welding, suturing, knitting, heat shrinkage by a heat shrink pipe, binding and fusion welding; and therefore, the multiple catching subrings 111 are connected together, and the catching sections 113 of the multiple catching subrings 111 together form the catching ring 11. It can be understood that in other embodiments, the catching ring 11 and the connecting rods 15 also may be integrated, and for example, they are formed by cutting a nickel-titanium tube or a stainless steel tube and shaping the cut tube, or a nickel-titanium piece or a stainless steel piece is cut into the catching ring 11 and the connecting rods 15 which are located in the same plane according to the desired parameters, or are cut and shaped into the catching ring 11 and the connecting rods 15 which are located in different planes.

It can be understood that in other embodiments, only one connecting rod of at least one catching subring in the multiple catching subrings of the catcher and the connecting rods of an adjacent catching subring at least partially share the edge; for example, if there are three catching subrings of the catcher, one catching subring in the three catching subrings includes one connecting rod, and two ends of the catching section of the catching subring including one connecting rod are respectively connected with two ends of the connecting rod; when the three catching subrings are connected into a whole, the catching subring including one connecting rod is located on the same sides of the other two catching subrings, and the connecting rod of the catching subring including one connecting rod and the connecting rods of the other two catching subrings at least partially share the edge; for another example, if there are two catching subrings of the catcher, each catching subring in the two catching subrings includes one connecting rod, and the connecting rods of the two catching subrings, each of which includes one connecting rod, at least partially share edges. It also can be understood that in other embodiments, the connecting rods in the catching subrings also may include straight sections, curved sections or polyline sections. It also may be understood that in other embodiments, the catching subrings also may be provided in rectangular, trapezoid or other irregular shapes.

Figure 6:
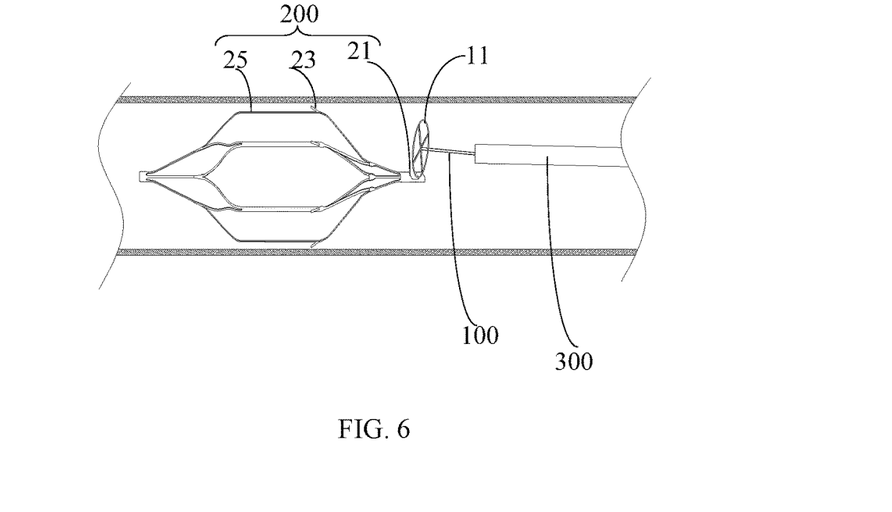
FIG. 6 is a schematic diagram showing the catching a filter by the catcher in FIG. 3.

With reference to FIG. 6, a process of catching the filter includes the following steps: first, the catching ring 11 of the catcher 100 is delivered to the to-be-caught filter 200 through a sheath 300, and returns from a compressed state during the delivery process into an expanded state; second, the catching subrings 111 of the catching ring 11 are connected to a withdrawing hook 21 of the filter 200 in a surrounding manner; then the catching ring 11 of the catcher 100 is pulled to the proximal end, and the moving catching ring 11 drives the filter 200 to be compressed into the sheath 300; and finally, the filter 200 is transplanted out of the body, thus completing the withdrawal of the filter 200.

The catching ring 11 of the catcher 100 of the present disclosure is of a ring structure supported by the connecting rods 15, thereby having a relatively high stability and is also resistant to deformation under erosion by blood flow, so as to facilitate accurate positioning by a doctor during clinical operations, and thereby increasing the success rate of withdrawal. In addition, the catching ring 11 of the catcher 100 of the present disclosure includes multiple catching subrings 111; and each catching subring 111 may be independently used for catching the vena cava filter 200. As the diameter of the surrounding circle of the catching ring 11 is 8 to 30 mm, under the limitation of the perimeter of a single catching subring 111, it is more difficult for the single catching subring 111 to catch a fixing anchor 23 or a supporting rod 25 of the vena cava filter 200 than a catching loop 400 in the prior art, thereby improving the safety of the clinical operations.

Figure 7:
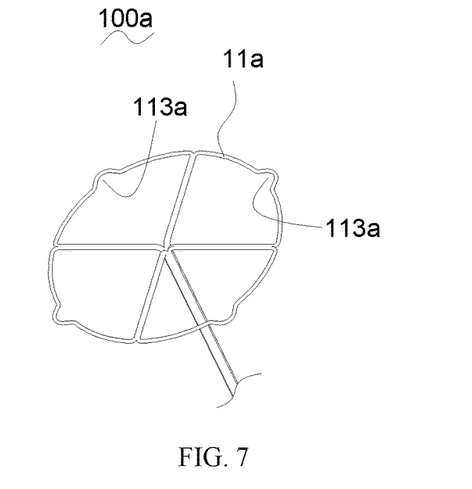
FIG. 7 is a schematic diagram of a catcher provided by another embodiment of the present disclosure.

With reference to FIG. 7, a catcher 100a provided by another embodiment of the present disclosure is approximately the same as the catcher 100, and includes a catching ring 11a, but the difference is that one portion of the catching ring 11a has an outward depression along a radial direction to form a catching groove 113a, During the process of catching a filter 200, the catching groove 113a achieves a more accurate positioning and firmer catching ability. In this embodiment, the catching ring 11a has four catching grooves 111a. It can be understood that in other embodiments, the catching ring 11a also may only have one catching groove 111a, and the number of the catching groove may be set based on any desired application or need.

Figure 8:
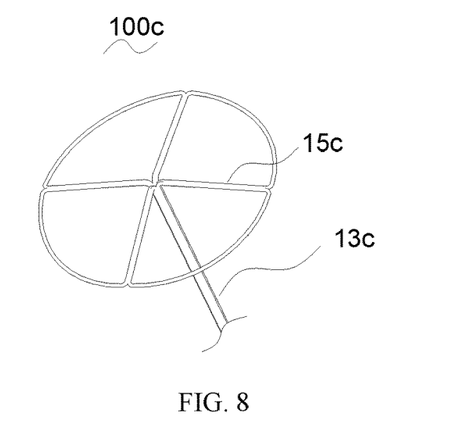
FIG. 8 is a schematic diagram of a catcher provided by another embodiment of the present disclosure.
Figure 9:
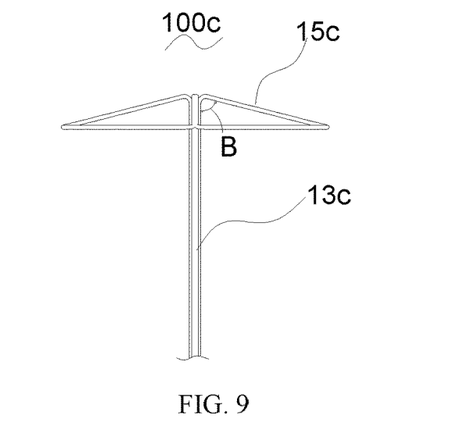
FIG. 9 is a side view of the catcher in FIG. 8.

With reference to FIG. 8 and FIG. 9, a catcher 100b provided by another embodiment of the present disclosure is approximately the same as the catcher 100, and includes connecting rods 15b and an operating rod 13b, but the difference is that an included angle B between a connecting line of two ends of each connecting rod 15a and the longitudinal central axial line of the operating rod 13b is 75 degrees.

Figure 10:
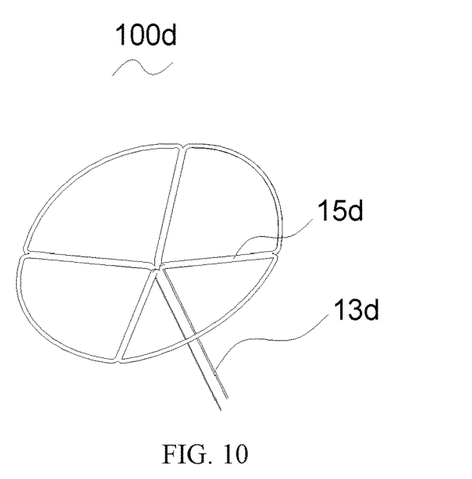
FIG. 10 is a schematic diagram of a catcher provided by another embodiment of the present disclosure.
Figure 11:
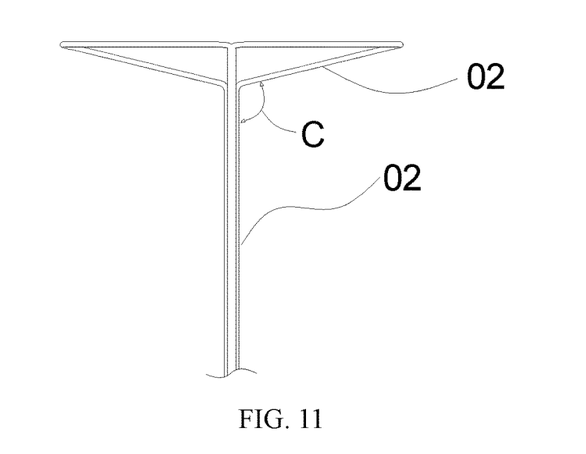
FIG. 11 is a side view of the catcher in FIG. 10.

With reference to FIG. 10 and FIG. 11, a catcher 100c provided by another embodiment of the present disclosure is approximately the same as the catcher 100, and includes connecting rods 15c and an operating rod 13c, but the difference is that an included angle C between a connecting line of two ends of each connecting rod 15c and the longitudinal central axial line of the operating rod 13c is 115 degrees.

Figure 12:
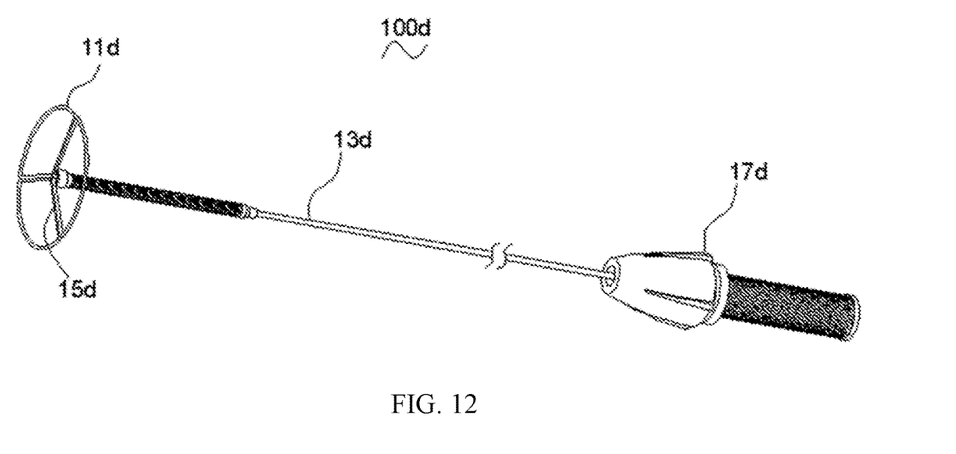
FIG. 12 is a schematic diagram of a catcher provided by another embodiment of the present disclosure.

With reference to FIG. 12, a catcher 100d provided by another embodiment of the present disclosure is approximately the same as the catcher 100, and includes a catching ring 11d, an operating rod 13d, connecting rods 15d and a handle 17d. The diameter of a surrounding circle of the catching ring 11d is 8 to 30 mm.

Figure 13:
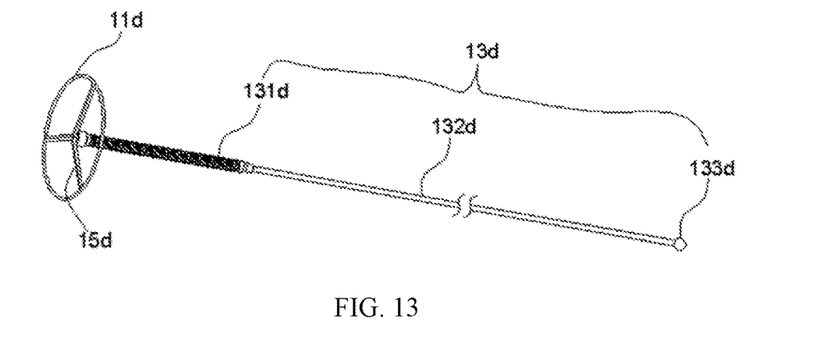
FIG. 13 is a schematic diagram of a partial structure of the catcher in FIG. 12.

With reference to FIG. 13, the operating rod 13d includes a soft section 131d connected with the catching ring 11d, an operating section 132d connected to the proximal end of the soft section 131d, and an anti-detachment part 133d fixedly arranged at the proximal end of the operating section 132d. Under the action of the same external force, the soft section 131d deforms more easily than the operating section 132d. The anti-detachment part 133d is spherical. In this embodiment, the soft section 131d is a spring pipe. It can be understood that the soft section 131d also may be made of a hypotube, a flexible plastic pipe, a spring or any other materials that are easier to deform than the operating section 132d, The soft section 131d and the catching ring 11d as well as the soft section 131d and the operating section 132d may be directly connected through a process such as welding, fusion welding, riveting, suturing, heat shrinkage by a heat shrink pipe and binding, or connected through mediums as long as their joints are capable of bearing a certain tensile force. In this embodiment, the soft section 131d is connected to a gathered position of the connecting rods 15d, and the soft section 131d is connected with the connecting rods 15d through welding.

Figure 14:
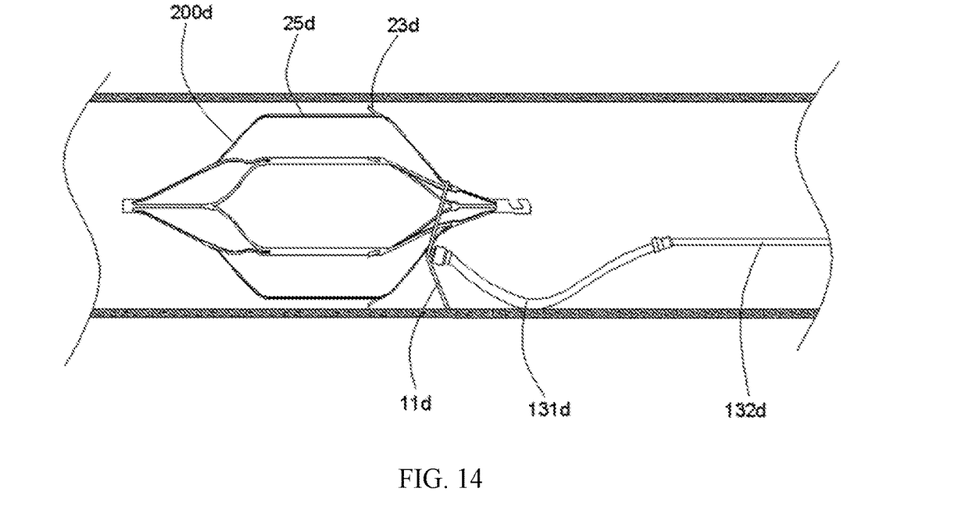
FIG. 14 is a schematic diagram showing the catching a filter by the catcher in FIG. 12.

During the process of catching a filter using a conventional catcher, when an operator pushes an operating rod to enable a catching loop to be connected with a withdrawing hook of the filter in a surrounding manner, the catching ring will compress the filter and move along the filter due to an extremely high pushing force, which leads to a situation that the catching ring grabs a fixing anchor or a supporting rod of the filter. However, with reference to FIG. 14, the catcher 100d of this embodiment has the soft section 131d, so that when the pushing force that pushes the operating rod 13d is extremely high, the soft section 131d will have a bending deformation under the pressure to ensure that the catching ring 11d will not continuously move forwards to compress the filter 200d, thereby reducing the possibility that the catching ring 11d grabs the fixing anchor 23d or the supporting rod 25d of the filter 200d, thereby improving the safety of the procedure.

It can be understood that the soft section 131d and the connecting rods 15d or the catching ring 11d also may be connected through a rigid section; and under the action of the same external force, the soft section 131d is easier to deform than the rigid section.

Figure 15:
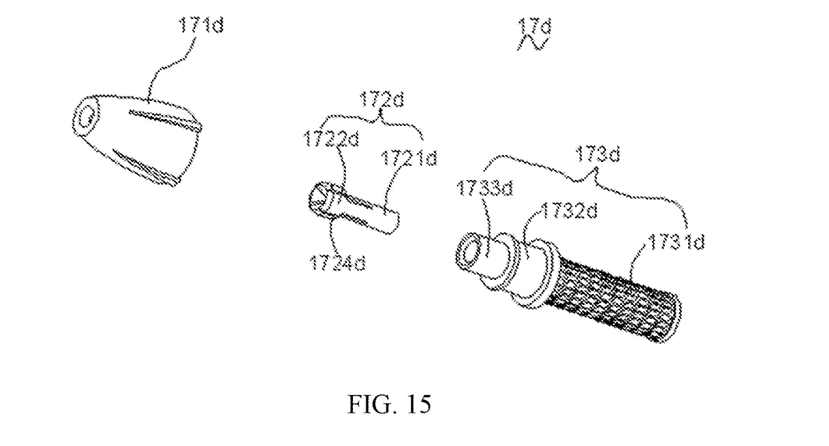
FIG. 15 is a schematic diagram of a handle of the catcher in FIG. 12.
Figure 16:
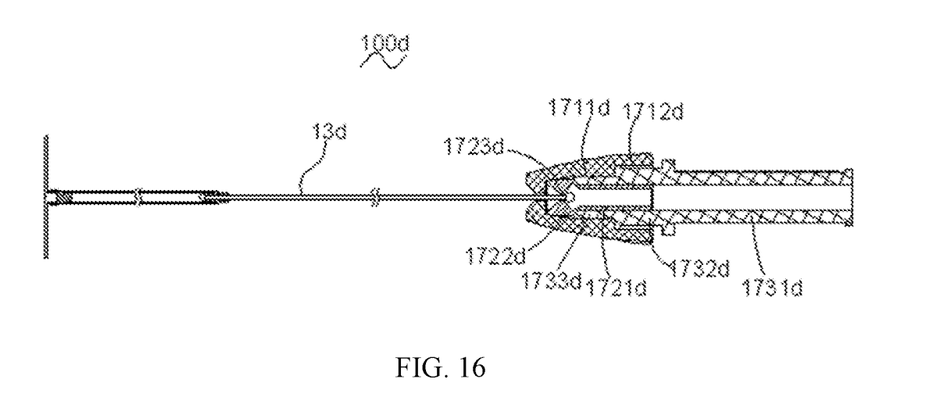
FIG. 16 is a profile view of the catcher in FIG. 12.

With reference to FIG. 15 and FIG. 16, the handle 17d includes a spiral part 171d, a clamping part 172d and a holding part 173d. The spiral part 171d has a hollow structure, and has an approximately step-like inner cavity; the step-like inner cavity includes a threaded inner cavity section 1712d which is close to the proximal end and is provided with an internal thread, and a truncated cone inner cavity section 1711d which is close to the distal end and has an inner diameter that gradually decreases from the proximal end to the distal end; a joint of the thread inner cavity section 1712d and the truncated cone inner cavity section 1711d forms a step in the inner cavity; in other words, the threaded inner cavity section 1712d communicates with the truncated cone inner cavity section 1711d, and the inner diameter of the distal end of the threaded inner cavity section 1712d is greater than that of the proximal end of the truncated cone inner cavity section 1711d. The outer diameter of the anti-detachment part 133d of the operating rod 13d is less than the minimum inner diameter of the spiral part 171d.

The holding part 173d has a hollow structure, and includes a holding portion 1731d, a threaded portion 1732d and an abutting portion 1733d which are interconnected in sequence and which extend from the proximal end to the distal end; and an external thread that matches with the internal thread of the spiral part 171d is formed on the threaded portion 1732d.

The clamping part 172d has a hollow structure, and includes a main body section 1721d and a clamping section 1722d arranged at the distal end of the main body section 1721d; and the outer diameter of the clamping section 1722d is greater than that of the main body section 1721d to form a step at a joint of the clamping section 1722d and the main body section 1721d. The inner wall of the clamping section 1722d extends towards the inside of the cavity to form a hollow annular boss 1723d. The thickness of the annular boss 1723d along an axial direction of the clamping part 172d is gradually reduced from outside to inside, so that the clamping section 1722d has a minimum inner diameter. Multiple slots 1724d which run through the inner cavity and extend along a lengthwise direction of the clamping part 172d are formed in the clamping portion 1722d and a portion, which is close to the clamping section 1722d, of the main body section 1721d, so that the inner diameter of the clamping section 1722d may be reduced under the pressure applied by the external force. When the clamping part 172d is in a natural state, the minimum inner diameter of the clamping section 1722d and the inner diameter of the main body section 1721d are both greater than the outer diameter of the anti-detachment part 133d, and the anti-detachment part 133d may move from the distal end of the clamping section 1722d to the inner cavity of the main body section 1721d; when the clamping part 172d is pressed by the external force, the inner diameter of the clamping section 1722d is reduced, and the minimum inner diameter of the clamping section 1722d is less than the outer diameter of the anti-detachment part 133d; and at the moment, the anti-detachment part 133d is prevented from passing through the annular boss 1723d of the clamping section 1722d during a process of moving from the inner cavity of the main body section 1721d to the distal end of the clamping section 1722d.

With reference to FIG. 16 again, during assembly of the catcher 100d, the anti-detachment part 133d of the operating rod 13d first penetrates into the inner cavity of the spiral part 171d from the distal end of the spiral part 171d, and then penetrates the clamping part 172d; second, the main body section 1721d of the clamping part 172d is inserted into the abutting portion 1733d of the holding part 173d, and the proximal end of the clamping section 1722d of the clamping part 172d abuts the distal end of the abutting portion 1733d of the holding part 173d; and then the spiral part 171d and the holding part 173d are screwed together in a threaded fit manner, and the truncated cone inner cavity section 1711d of the spiral part 171d presses the clamping section 1722d of the clamping part 172d, so that the inner diameter of the clamping section 1722d is reduced, thereby fixing the anti-detachment part 133d in the clamping part 172d through the annular boss 1723d.

The operating rod 13d and the handle 17d of the catcher 100d of this embodiment are connected through the anti-detachment part 133d and the clamping part 172d to prevent mutual sliding between the operating rod 13d and the handle 17d and even separation of the operating rod 13d from the handle 17d due to extremely high withdrawal force, so that the success rate of withdrawal is increased.

It can be understood that the anti-detachment part 133d may also have a square shape, an elongated shape, a triangular shape or any other shapes capable of cooperating with the clamping part 172d to play a stopping role.

It can be understood that the operating rod 13d does not need to include the anti-detachment part 133d, so that the operating section 132d directly penetrates into the inner cavity of the spiral part 171d, and is clamped by the annular boss 1723d.

It can be understood that the handle 17d does not need to include the spiral part 171d and the holding part 173d, namely it is possible for the handle 17d to only include the clamping part 172d as long as there is a radial external force clamping the clamping part 172d during operation of the handle 17d to reduce the inner diameter of the clamping section 1722d to clamp the operating rod 13d.

The above-mentioned embodiments are merely expressive of several implementation modes of the present disclosure, and their descriptions are relatively specific and detailed, but not deemed as limiting the scope of patent of the present disclosure. It should be noted that ordinary persons skilled in the art can make a plurality of transformations and improvements that all fall within the scope of protection of the present disclosure without departing from the scope of the present disclosure. Therefore, the scope of protection of patent of the present disclosure shall be based on attached claims.

The invention claimed is:

1. In combination:
   a filter;
   a filter retriever, comprising:
   a catching ring that has a periphery;
   a plurality of connecting rods, each connecting rod having a first end that is connected with the catching ring, and a second end, with the second ends of the plurality of connecting rods being gathered together, and wherein all the plurality of connecting rods are located in the same plane;
   wherein the plurality of connecting rods and the catching ring define a plurality of adjacent catching subrings, where the connecting rods of two adjacent catching subrings at least partially share one edge, and the multiple catching subrings form the catching ring; and
   wherein after the catching ring is connected to the filter, the catching ring will move the filter out of a human body.

2. The combination of claim 1, wherein the retriever also comprises an operating rod having a distal end and a proximal end, and the second ends of all the connecting rods are gathered together at the distal end of the operating rod.

3. The combination of claim 1, wherein the operating rod has a soft section adjacent the distal end, and an operating section adjacent the proximal end of the operating rod, the soft section having a proximal end, and the operating section is connected to the proximal end of the soft section, and wherein the soft section is more flexible than the operating section.

4. A filter retriever, comprising:
   a catching ring that has a periphery;
   a plurality of connecting rods, each connecting rod having a first end that is connected with the catching ring, and a second end, with the second ends of the plurality of connecting rods being gathered together, and wherein all the plurality of connecting rods are located in the same plane;
   wherein the plurality of connecting rods and the catching ring define a plurality of adjacent catching subrings, where the connecting rods of two adjacent catching subrings at least partially share one edge, and the multiple catching subrings form the catching ring;
   wherein the retriever also comprises an operating rod having a distal end and a proximal end, and the second ends of all the connecting rods are gathered together at the distal end of the operating rod;

wherein the operating rod has a soft section adjacent the distal end, and an operating section adjacent the proximal end of the operating rod, the soft section having a proximal end, and the operating section is connected to the proximal end of the soft section, and wherein the soft section is more flexible than the operating section; and wherein a projection of the catching ring on a section perpendicular to a lengthwise direction of the operating rod surrounds a projection of the distal end of the operating rod on the same section.

5. The retriever of claim 4, wherein the first and second ends of each connecting rod define a connecting line that is located within the periphery of the catching ring.

6. The retriever of claim 4, wherein the plurality of connecting rods and the catching ring are located in the same plane, the catching ring is a circular ring, and a connecting line formed by the first and second ends of each connecting rod forms a radius of the catching ring.

7. The retriever of claim 4, wherein the plurality of connecting rods and the catching ring are located in the same plane, the catching ring is an elliptical ring, and a connecting line formed by the first and second ends of each connecting rod forms a long axis or a short axis of the catching ring.

8. A filter retriever, comprising:
a catching ring that has a periphery;
a plurality of connecting rods, each connecting rod having a first end that is connected with the catching ring, and a second end, with the second ends of the plurality of connecting rods being gathered together, and wherein all the plurality of connecting rods are located in the same plane;
an operating rod having a distal end, a proximal end, a soft section adjacent the distal end and having a proximal end, and an operating section adjacent the proximal end of the operating rod and connected to the proximal end of the soft section, and wherein the soft section is more flexible than the operating section;
wherein all the second ends of all the connecting rods are gathered together and connected at the distal end of the operating rod; and
wherein the soft section is a spring pipe with the operating section made from a different material as the soft section.

9. The retriever of claim 8, wherein the proximal end of the operating section is directly connected to the proximal end of the soft section.

10. The retriever of claim 9, wherein the plurality of connecting rods and the catching ring define a plurality of adjacent catching subrings, where the connecting rods of two adjacent catching subrings at least partially share one edge, and the multiple catching subrings form the catching ring.

11. The retriever of claim 8, wherein:
the first and second ends of each connecting rod define a connecting line that is located within the periphery the catching ring.

12. The retriever of claim 11, wherein the plurality of connecting rods and the catching ring define a plurality of adjacent catching subrings, where the connecting rods of two adjacent catching subrings at least partially share one edge, and the multiple catching subrings form the catching ring.

13. The retriever of claim 8, wherein the soft section has a distal end that is connected to the second ends of the plurality of connecting rods.

14. The retriever of claim 8, wherein the operating section has a proximal end, and the operating rod also comprises an anti-detachment part arranged at the proximal end of the operating section.

15. The retriever of claim 14, further comprising a handle connected to the proximal end of the operating rod, the handle comprising a clamping part arranged at the proximal end of the operating rod, the clamping part comprising:
a main body section having a distal end, and an inner cavity;
a hollow clamping section which is arranged at the distal end of the main body section and having an inner cavity which communicates with the inner cavity of the main body section, the clamping section having an inner diameter, and wherein the inner cavity of the clamping section has a distal end and a proximal end;
wherein the main body section and the hollow clamping section have multiple slots formed therein which communicate with the inner cavity;
wherein in a natural state, the anti-detachment part may move from the distal end of the inner cavity of the clamping section to the proximal end of the inner cavity of the clamping section; and under the action of a radial external force, the inner diameter of the clamping section is reduced; and the anti-detachment is not separated from the clamping section when being clamped by the clamping section.

16. The retriever of claim 15, wherein the clamping section has an inner wall, and the inner wall of the clamping section extends towards the inner cavity of the clamping section to form a hollow annular boss, the annular boss having a length along an axial direction of the clamping section that is reduced successively from outside to inside, and under the action of the radial external force, the anti-detachment part is not separated from the annular boss when being clamped by the annular boss.

17. The retriever of claim 1, wherein each connecting rod is a straight rod between its first and second ends.

18. The retriever of claim 4, wherein each connecting rod is a straight rod between its first and second ends.

19. The retriever of claim 8, wherein each connecting rod is a straight rod between its first and second ends.

20. The retriever of claim 15, wherein the anti-detachment part is spherical.

* * * * *